| United States Patent [19] | [11] Patent Number: 4,917,884 |
| Roberts | [45] Date of Patent: Apr. 17, 1990 |

[54] SHAVING COMPOSITIONS

[76] Inventor: David Roberts, 7242 Mission Hill Dr., Las Vegas, Nev. 89113

[21] Appl. No.: 149,122

[22] Filed: Jan. 27, 1988

[51] Int. Cl.$^4$ ................................................ A61K 7/15
[52] U.S. Cl. ...................................... 424/73; 514/772
[58] Field of Search ........................... 424/73; 514/772

[56] References Cited

U.S. PATENT DOCUMENTS

| 1,979,385 | 11/1934 | Harvey, Jr. | 424/73 |
| 2,129,836 | 2/1936 | Goodman | 424/73 |
| 2,987,446 | 6/1961 | Riethmüller | 424/73 |
| 3,650,280 | 3/1972 | Roberts et al. | 424/81 X |
| 4,752,620 | 6/1988 | Roberts | 514/588 |

*Primary Examiner*—Thurman K. Page
*Assistant Examiner*—Susan S. Rucker
*Attorney, Agent, or Firm*—Morgan & Finnegan

[57] ABSTRACT

A novel shaving composition containing glyoxal, urea and soaping compositions for providing excellent lubrication and conditioning for facial hair areas. The compositions of this invention are stable over an indefinite period of time. Addition of an aged diethyleneglycol monoethyl ether composition which is believed to be oxidized allows the compositions to remain potent and stable over an indefinite time period.

19 Claims, No Drawings

SHAVING COMPOSITIONS

This invention relates to a novel shaving composition. The novel compositions of this invention contain glyoxal, urea and soaping compositions and provide excellent lubrication and conditioning for facial hair areas. The compositions of this invention are stable over an indefinite period of time. The addition of an aged diethyleneglycol monoethyl ether composition which may be oxidized allows the compositions to remain potent and stable over an indefinite time period.

BACKGROUND OF THE INVENTION

Shaving compositions for shaving facial hair areas have varied over the years from powders mixed with hot water, "brushless" shaving creams dispensed from tubes, and aerosol foam shaving compositions dispensed from cans. Each of the compositions suffers from one or more drawbacks. Some are inconvenient to use, others fail to provide adequate protection of skin during shaving and still others do not prepare the hair and hair area for effective trimming of hair material. Shaving compositions of the present invention are convenient to use, protect the skin, and prepare the hair for effective trimming, thereby providing a clean, smooth, comfortable shave.

Urea and glyoxal compositions for use in the cosmetic treatment of hair were described in U.S. Pat. No. 3,650,280, which is incorporated herein by reference. These compositions aid in beautifying hair. They were not known to be useful as a facial hair shaving composition Furthermore, it was found that these compositions were stable for a relatively limited period of time. After six weeks, they developed hard crystalline lumps and lost the quality of their consistency. Therefore, they could not be used for their intended purpose after a relatively short period of time. The lumps and crystals needed to be separated from the remainder of the compositions in order to produce a product with good textural characteristics.

The inventor has found, unexpectedly, that the addition of soap-type additives such as palmitic acid and triethanolamine render the compositions set forth in U.S. Pat. No. 3,650,280 capable for use as shaving compositions which have unexpected and novel advantages over other shaving compositions.

It is, therefore, an object of this invention to provide compositions for use in shaving facial hair.

Another object of this invention is to provide improved compositions for use in shaving facial hair which may be used after long periods of storage.

It is another object of, this invention to provide a method for using a glyoxal composition, diethyleneglycol monoethyl ether which has been aged and may be oxidized.

Yet another object of this invention is to provide a facial hair shaving composition which maintains a smooth creamy texture and maximum potency over the duration of its storage and use.

DESCRIPTION OF THE INVENTION

Surprisingly, with the addition of soaping factors, the compositions set forth in U.S. Pat. No. 3,650,280 can be used in the facial shaving process. The compositions of this invention are a great improvement over prior art compositions. They provide lubrication of the face during the shaving process and leave a coating on the face after it is dried. If rewet with water, the lubricating action of the compositions of this invention is reactivated and the face can continue to be shaved without reapplying the shaving compositions.

Upon application, the compositions set hair up and react with the hair to soften it. Preparation of the hair in this manner makes shaving easier, eliminates nicks and cuts that frequently occur with other shaving compositions, and extends the useful life of a razor blade such that a single blade edge may be used more than 30 times. In most circumstances, the composition is applied and, after a few seconds, shaving is begun. For tough beards, the compositions should be allowed to settle into the beard and react with it for about one minute prior to commencement of shaving.

In addition, the compositions of this invention have the characteristics that they contain aged diethyleneglycol monoethyl either that may be oxidized and may be made by aging the compound over a relatively long period of time, by heating the compound or by any other method known to those of skill in the art.

Preferably, a diethyleneglycol monoethyl ether manufactured and distributed by Union Carbide Corporation, Carbitol, is used in the diethyleneglycol monoethyl ether fraction. The diethyleneglycol monoethyl ether should be allowed to oxidize until it becomes cloudy and reddish-tan in color, generally a time period of about three to about six months. It is believed that there is in the oxidized Carbitol a metal which may contribute to preserving and creating a shelf-life for the composition. The metal may be oxidized iron from the containers of the diethyleneglycol monoethyl ether.

Preferred compositions which have soap-type additives such as fatty acids and alkanolamines, and which have unexpected and novel advantages over other shaving compositions contain the following:

a. from about 0.08 to about 9 percent by weight of glyoxal;

b. from about 0.08 to about 9 percent by weight of urea;

c. from about 1.0 to about 2 percent by weight of oxidized diethyleneglycol monoethyl ether;

d. from about 8.5 to about 12.5 percent by weight of a fatty acid;

e. from about 3.0 to about 5.0 percent by weight of an alkanolamine; and f. as an inert carrier, water, a lower alkanol, or a mixture of water and a lower alkanol.

A critical feature of the composition of the present invention is that the ratio of amount of alkanolamine to amount of fatty acid is between about 1:2 and 1:3, preferably about 1:2.65. Ratios outside the critical range make the resulting product unsuitable for producing shaving/conditioning results which are achieved with compositions of this invention.

More preferred compositions will contain between about 9.5 and 11.5 percent and more preferably about 10.4 percent by weight of fatty acid. More preferred compositions will also contain between 3.5 and 4.5 percent and more preferably about 3.9 percent by weight of alkanolamine.

Preferred fatty acids are within the range of those having about 14 and about 20 carbon atoms. More preferred fatty acids are stearic and palmitic. Palmitic acid is most preferred.

Preferred alkanolamines are within the range of those having 2 to about 6 carbon atoms. More preferred alkanolamines are diethanolamine and triethanolamine. Triethanolamine is most preferred.

Another preferred composition will also contain a minor proportion (from about 1.0 to about 2 percent by weight) of benzyl alcohol.

There is nothing critical about the manner in which the shaving compositions of this invention are prepared. Those skilled in the art of formulating shaving compositions will be well aware of the manipulative techniques needed to provide the composition in the form of solutions, dispersions, lotions, gels, creams and the like. Preferred formulations will be exemplified in detail hereinafter. In one method, the liquid ingredients are blended, then the solids are mixed in. In another method powdered solids, e.g., urea and solid additives are mixed together first, then blended with part of the inert cosmetic carrier, then the liquid components, e.g., glyoxal, and the benzyl alcohol and oxidized diethyleneglycol monoethyl ether, if used, and opacifier, and other liquid additives, if desired, are blended with the reserved part of the cosmetic carrier, then final blending is made. In another method, the fatty acid, e.g stearic acid, is melted and mixed with liquid triethanolamine. The resulting liquid mixture is then added as described above. If necessary, the pH is adjusted in the final product to the desired non-alkaline level by adding the required amount of acid, e.g., hydrochloric acid, or alkali, e.g., sodium hydroxide solution.

The present formulations can be applied to the face or other area which one desires to shave by any method satisfactory to accomplish the desired purpose.

When used herein and in the appended claims, the term "non-alkaline" contemplates compositions in which the pH is from neutrality to acidic, i.e., about pH 7 or below. Excluded, of course, are media too acidic to be employed on the hair or skin without imparting damage. In any event, alkaline media, i.e., those of above pH 7 are excluded, and especially those alkaline pH's used commonly in hair waving compositions (wherein the optimum seems to be about pH 9.2). In the present non-alkaline compositions, the optimum pH for most purposes appears to be from about 4 to about 6.

The urea and glyoxal ingredients used in the present compositions are items of commerce. They have been found to be essential. It is not possible to use either urea or glyoxal alone to obtain the desired results. Preferably, unpurified glyoxal, such as that available from American Hoechst Co., used alone. However, a remarkable penetrating, swelling and surrounding of the outer structure of hair is seen if the hair is treated with urea and glyoxal used together under non-alkaline conditions in an inert cosmetic carrier.

Suitable carriers comprise a class of nonirritating liquids which may be safely applied to the skin and hair of mammals, such as water, alcohols, especially lower alcohols of from two to six carbon atoms, e.g., ethanol, isopropanol, etc., mixtures of water and lower alcohols, fats, such as lanolin, and the like.

The ratio of the combined volume or weight of urea and glyoxal to the volume or weight of carrier used is not particularly critical Suitable formulations depending on the end use contemplated can be prepared easily by those skilled in the art. Generally, for economic reasons, and for ease of application, the composition will contain a minor proportion, i.e., less than 50 percent by weight of urea, glyoxal, and oxidized diethyleneglycol monoethyl ether and a major proportion of carrier. Preferably, the ratio of glyoxal to urea will be approximately 1:1. For most purposes, the best properties will be obtained with compositions containing from about 0.04 to about 8 percent and preferably from about 0.04 to about 8 percent by weight of glyoxal and from about 0.1 to about the solubility limit in water, but preferably from about 0.20 to about 9 percent of urea.

The addition of benzyl alcohol or aged diethylene glycol monoethyl ether to the basic formulation, in minor proportions, e.g., either or both together providing less than 50 percent by weight of the final composition, enhances the properties of the instant compositions. Compositions containing either of these ingredients or, preferably both of them, are important embodiments hereof. Benzyl alcohol in minor proportions, e.g., especially from about 0.1 to about 4 percent by weight, and preferably from about 0.1 to about 2 percent by weight in the composition seem to facilitate penetration and reduce the time required to obtain the desired results.

In addition to increasing the shelf-life and improving the texture of the composition, the aged diethylene glycol monoethyl ether appears to facilitate penetration and reduce the time required to obtain the desired results as well.

Of course, as will be obvious to those skilled in the art, a variety of conventional additives may be used in the instant compositions to secure additional objectives. For example, small amounts of stabilizers and sequestrants, e.g., sorbic acid or its salts; gelling agents, such as polythers; opacifiers; hydrolyzed proteins; perfumes and the like, may be used. Also, pigments and antiseptics and the like can be added. These additives will comprise generally a minor proportion of the compositions, e.g., up to about 2 percent by weight in the most preferred formulations.

With the addition of aged diethylene glycol monoethyl ether, the formulations of this invention remain smooth and creamy throughout their life. Prior to the addition of aged diethylene glycol monoethyl ether, the formulations tended to crystallize and form unasthetic and unusable lumps over a period of time.

With the presence of fatty acid and alkanolamine, these compositions are suitable for shaving and simultaneously conditioning the skin. The composition is an antibacterial formulation in the sense that the composition protects the skin and keeps it from blemishing. The composition is a low-foam, clear product such that you can see beard while shaving.

DESCRIPTION OF THE PREFERRED EMBODIMENTS

Preferably, the aged diethylene glycol monoethyl ether composition should have approximately the following physical properties:

| Specific Gravity at 20° C. | 1.026 |
| --- | --- |
| Distillation | |
| Initial Boiling Point | 186° C. |
| 93% distilled | 196° C. |
| Dry Point | 199° C. |
| Acidity, % as acetic acid | 0.011% |
| Water | 0.26% |
| Odor | Slight, mild |
| Suspended Matter | None noticeable |

An increased acidity relative to unaged diethylene glycol monoethyl ether is believed to contribute to the preservation of the composition and create a shelf-life.

The oxidized diethylene glycol monoethyl ether additive of this invention may be made by allowing a diethylene glycol monoethyl ether additive to age and thereby oxidize over a period of time at room temperature. This process generally takes between about three and about six months. The composition should be allowed to age, or oxidize, until its appearance is cloudy and reddish-tan in color. This aging process may also be accelerated by heating or by other means known to those of ordinary skill in the art.

It is believed that the increase in acetic acid aids in the preservation of the shaving compositions of this invention. It is also believed that the aging of the ether compound to acetic acid may be simulated by addition of acetic acid. However, the pH of shaving composition should be adjusted after preparation in order to ensure appropriate pH value for use on the hair and skin.

The following examples describe the preparation of compositions according to the present invention.

EXAMPLE 1

Compositions having the following formulation, expressed in parts by weight, are prepared.

| | |
|---|---|
| glyoxal | 1–4 |
| urea | 1–4 |
| aged diethyleneglycol mono ethyl ether additive | 1–2 |
| benzyl alcohol | 1–2 |
| palmitic acid | 9–12 |
| triethanolamine | 3–5 |
| water q.s | 100.00 |

These compositions are used as shaving compositions for lubrication and skin protection, and should remain potent indefinitely.

Although specific embodiments of the invention have been described herein, it is obvious that many variations will suggest themselves to those skilled in the art after reading this detailed description. It is intended to include all obvious variations and modifications within the spirit and scope of the appended claims.

EXAMPLE 2

A composition having the following formulation, expressed in parts by weight, is prepared.

| | |
|---|---|
| palmitic acid | 10.455 |
| triethanolamine | 3.938 |
| glyoxal | 1.712 |
| urea | 1.712 |
| aged diethyleneglycol mono ethyl ether | 1.712 |
| benzyl alcohol | 1.712 |
| carboxy polymethylene | 0.771 |
| formalin | 0.214 |
| sodium hydroxide | 0.150 |
| hydrolyzed protein | 0.086 |
| polyvinylpyrrolidone | 0.043 |
| perfume | q.s. |
| opacifier | q.s. |
| water | q.s. |
| | 100.0 |

What is claimed is:

1. An improved shaving composition consisting essentially of aged diethyleneglycol monoethyl ether, glyoxal, urea, fatty acid and alkanolamine, wherein the ratio by weight of alkanolamine to fatty acid is between about 1:2 and about 1:3.

2. A composition according to claim 1 wherein said aged diethyleneglycol monoethyl ether composition has a specific gravity of 20 C of 1.025, an initial boiling point during distillation of 186 C, 93% distillation point of 196 C, a dry point of 199 C, acidity (% as acetic acid) of 0.011%, contains 0.26% water, has a slight, mild odor and no noticeable suspended matter.

3. A composition according to claim 1 wherein said aged diethyleneglycol monoethyl ether composition was made by allowing a diethyleneglycol monoethyl ether composition to age over a period of about three to about six months.

4. A composition according to claim 1 wherein said aged diethyleneglycol monoethyl ether composition is reddish-tan in appearance.

5. A composition according to claim 1 wherein said aged diethyleneglycol monoethyl ether composition was made by heating a diethyleneglycol monoethyl ether composition.

6. A composition according to claim 1 wherein the ratio by weight of fatty acid to alkanolamine is about 2.65:1.

7. A composition according to claim 1 wherein the ratio of the weight of fatty acid and alkanolamine, combined, to the weight of aged diethyleneglycol monoethyl ether, glyoxal and urea, combined, is between about 5.6:1 and about 1.3:1.

8. A shaving composition consisting essentially of:
   a. from about 0.08 to about 9 percent by weight of glyoxal;
   b. from about 0.08 to about 9 percent by weight of urea;
   c. from about 1.0 to about 2 percent by weight of aged diethyleneglycol monoethyl ether;
   d. from about 8.5 to about 12.5 percent by weight of a fatty acid;
   e. from about 3.0 to about 5.0 percent by weight of an alkanolamine; and
   f. as an inert carrier, water, a lower alkanol, or a mixture of water and a lower alkanol;
wherein the ratio by weight of alkanolamine to fatty acid is between about 1:2 and about 1:3.

9. A shaving composition according to claim 8 wherein said composition has a shelf-life of more than one year.

10. A composition according to claim 8 wherein the fatty acid is present in an amount between about 9.5 and 11.5 percent.

11. A composition according to claim 8 wherein the fatty acid is present in an amount of about 10.4 percent.

12. A composition according to claim 8 wherein the alkanolamine is present in an amount between about 3.5 and 4.5 percent.

13. A composition according to claim 8 wherein the alkanolamine is present in an amount of about 3.9 percent.

14. A composition according to claim 8 wherein the alkanolamine is triethanolamine.

15. A composition according to claim 8 wherein the fatty acid is palmitic acid.

16. A composition according to claim 8 wherein the fatty acid is stearic acid.

17. An improved shaving composition consisting essentially of:
   a. from about 1 to 4 parts by weight of glyoxal;
   b. from about 1 to 4 parts by weight of urea;

c. from about 1 to 2 parts by weight of aged diethyleneglycol monoethyl ether additive;
d. from about 1 to 2 parts by weight of benzyl alcohol;
e. from about 9 to 12 parts by weight of palmitic acid;
f. from about 3 to 5 parts by weight of triethenolamine; and
g. the balance consisting essentially of water;
wherein the ratio by weight of alkanolamine to fatty acid is between about 1:2 and about 1:3.

18. An improved shaving composition consisting essentially of:
a. about 10.5 parts by weight of palmitic acid;
b. about 3.9 parts by weight of triethanolamine;
c. about 1.7 parts by weight of glyoxal;
d. about 1.7 parts by weight of urea;
e. about 1.7 parts by weight of aged diethyleneglycol mono ethyl ether;
f. about 1.7 parts by weight of benzyl alcohol;
g. about 0.8 parts by weight of carboxy polymethylene;
h. about 0.2 parts by weight of formalin;
i. about 0.15 parts by weight of sodium hydroxide;
j. about 0.09 parts by weight of hydrolyzed protein;
k. about 0.04 parts by weight of polyvinylpyrrolidone; and
l. the balance consisting essentially of, perfume, opacifier and water.

19. A method of lubricating and conditioning hair prior to shaving, comprising applying to said hair a composition as defined in claim 1.

* * * * *